United States Patent [19]

Casey et al.

[11] Patent Number: 5,462,055
[45] Date of Patent: Oct. 31, 1995

[54] MRI/HYPERTHERMIA DUAL FUNCTION ANTENNA SYSTEM

[75] Inventors: James A. Casey, Smithtown; Robert E. McGill, Dix Hills, both of N.Y.

[73] Assignee: Northrop Grumman Corporation, Los Angeles, Calif.

[21] Appl. No.: 294,500

[22] Filed: Aug. 23, 1994

[51] Int. Cl.⁶ ............................................. A61B 5/055
[52] U.S. Cl. .................... 128/653.5; 128/736; 324/315; 324/322; 607/102; 607/156
[58] Field of Search ................. 128/653.2, 653.5, 128/736; 607/101, 102, 154, 156; 324/315, 318, 322

[56] References Cited

U.S. PATENT DOCUMENTS

| | | | |
|---|---|---|---|
| 5,109,853 | 5/1992 | Taicher et al. | 128/653.2 |
| 5,131,392 | 7/1992 | Jolesz et al. | 128/653.2 |
| 5,284,144 | 2/1994 | Delannoy et al. | 128/653.2 |
| 5,323,778 | 6/1994 | Kandarpa et al. | 128/653.2 |

*Primary Examiner*—Ruth S. Smith
*Attorney, Agent, or Firm*—Terry Anderson; Karl J. Hoch, Jr.

[57] ABSTRACT

An MRI machine RF body coil is arranged so that it can also function as a hyperthermia treatment apparatus by arranging the RF body coil as an array of individual antenna element connected to each other by individually controllable switches and feedthrough elements.

4 Claims, 4 Drawing Sheets

MRI/HYPERTHERMIA DUAL FUNCTION ANTENNA SYSTEM

BACKGROUND FOR THE INVENTION

1. Field of the Invention

This invention relates to a hyperthermia treatment apparatus and method, and more particularly to a hyperthermia apparatus and method in which radio frequency (RF) energy is directed at a subject tissue by axially polarized dipole antennas, and a magnetic resonance imaging (MRI) machine is used to monitor the temperature of the targeted and surrounding tissues during treatment.

2. Description of Related Art

The goal of hyperthermia treatment is the destruction of tumors by raising their temperatures for an extended period of time. When certain cancerous tumors are treated by raising the temperature of the tumors to approximately 43° C. for periods of 30–60 minutes via the process of hyperthermia, those tumors have been shown to be more susceptible to the effects of radiation and chemotherapy.

The treatment relies on the primitive nature of tumor vasculature. Tumor vasculature is less able than the vasculature of normal tissues to vasodilate in response to thermal stress, and thus cannot carry away heat efficiently. If tissue temperature remains elevated for an extended period of time, DNA synthesis is reduced, cell respiration is depressed, irreversible destruction of structure (and thus function) of chromosome associated proteins can occur, and autodigestion by the cells digestive mechanism can result.

Although the bioheat transfer mechanism in the body permits healthy tissue to regulate its temperature more efficiently than tumor tissue, precise control and monitoring of the treatment is still required to ensure that damage to the healthy tissue is minimized. In order for the hyperthermia process to be safe and effective, the heating during a hyperthermia procedure must be localized in the tumor volume to the maximum extent possible, and must also be uniform across that tumor volume. Particularly in cases where hyperthermia is used as an adjunct to radiation therapy and chemotherapy, significant hyperthermia to adjacent normal structure should be avoided in order to prevent hypersensitizing the healthy tissue to radiation and/or drugs. It is also essential that the heating be almost uniform within the tumor volume being treated. Relative cool spots during treatment may result in failure to kill certain cells, and perhaps a selection of cells with thermal tolerance.

The ideal power distribution for hyperthermia, therefore, is a pattern that provides broad, uniform heating over the entire treatment volume with a rather short drop-off at the tumor margins. In order to provide such a pattern, it has been proposed to use a whole body antenna array which operates at frequencies in the RF band which are capable of achieving deep penetration of the subject, and to non-invasively monitor the treatment using either a CT scanner or an MRI machine.

U.S. patent application Ser. No. 08/228,348 filed Apr. 15, 1994 (Button, Barbour, Cermignani, and Spacht), for example, discloses a hyperthermia system which combines a cylindrical phased array of axially polarized RF antennas for precise control of power distribution to the treatment area, with an MRI machine for non-invasively measuring temperatures of the targeted area during treatment. The system uses the non-invasive temperature measurement as a monitoring and feedback mechanism to increase procedural effectiveness and patient safety by allowing the operator to determine whether uniform heating is occurring in the target area, and to ensure that stray heating is not occurring in other areas.

While the system disclosed by Button et al. appears to represent a significant improvement over prior systems, it is difficult to implement in practice using conventional hyperthermia and MRI antenna arrangements. The problem is that conventional MRI machines are not designed to accommodate an entire RF antenna in addition to the RF body coil required in order to supply RF energy for the resonance process. Not only must the conventional machine be modified to accommodate the hyperthermia applicator, but the control circuitry of the conventional machine must be modified to switch between the two discrete antennas, each of which has different operating requirements and a different structure. Magnetic resonance imaging requires uniform application of very specific frequencies at relatively low energy across the area to be imaged, while hyperthermia treatment requires more focused application of energy sufficient to cause heating, which means that the RF antenna structure for the imaging portion of the treatment process is different in structure than the phased array antenna used for hyperthermia treatment. Thus, it has been assumed that dual antennas were needed in order to implement hyperthermia treatment with MRI monitoring. Because it is virtually impossible in conventional MRI machines to fit both antennas within the space provided for the single conventional MRI RF antenna, and in view of the high cost of the machines, it is unlikely that a significant number of providers will be able to make the necessary modifications or replace their existing MRI machines so as to include separate hyperthermia treatment antennas of the above-noted type, despite the advantages of hyperthermia treatment, unless some way of fitting the hyperthermia antenna into the existing machine can be found without requiring significant modifications to be made to the machine.

SUMMARY OF THE INVENTION

It is accordingly a first objective of the invention to overcome the disadvantages of the prior art by providing a hyperthermia treatment antenna array which can easily be retrofitted onto existing MRI machines, without the need for making significant modification to the machines.

It is a second objective of the invention to provide a combined antenna which includes both an MRI RF antenna of standard configuration and a hyperthermia applicator made up of a cylindrical phased array of axially polarized antennas.

It is a third objective of the invention to provide an apparatus for providing measured deep thermal doses to a specified treatment volume with controlled power distribution while at the same time permitting real time monitoring of tissue temperatures during treatment, and yet which can easily be retrofitted onto existing MRI machines by replacing the standard MRI RF antenna with a combined antenna having the same profile as the standard antenna.

These objectives are accomplished by providing an array of antenna elements connected to each other through mode switches and feedthroughs in such a manner that, by operating the switches, the same antenna elements can be rapidly configured for 1.) applying focused RF energy, and 2.) applying magnetic resonance imaging excitation energy.

More specifically, the invention provides a plurality of antenna elements connected to each other through controllable mode switches and RF feedthroughs so that, when the mode switches are switched on, all of the antenna elements are connected together in a whole body configuration which is supplied with RF energy at the appropriate MRI frequency, as in a conventional MRI machine, and when the mode switches are closed and the RF feedthroughs are switched on, the antenna elements are separated from each other and selectively connected to a source of hyperthermia energy to form axially polarized dipole antennas for applying hyperthermia energy to a targeted treatment area.

The invention thus provides a standard sized whole body MRI RF antenna coil dimensioned to fit around the body of the patient to be treated, but which can be rapidly switched to form a cylindrical phased array of individual dipole antennas capable of applying focused hyperthermia energy to a targeted tissue.

DETAILED DESCRIPTION OF THE PREFERRED EMBODIMENTS

Figure 1:
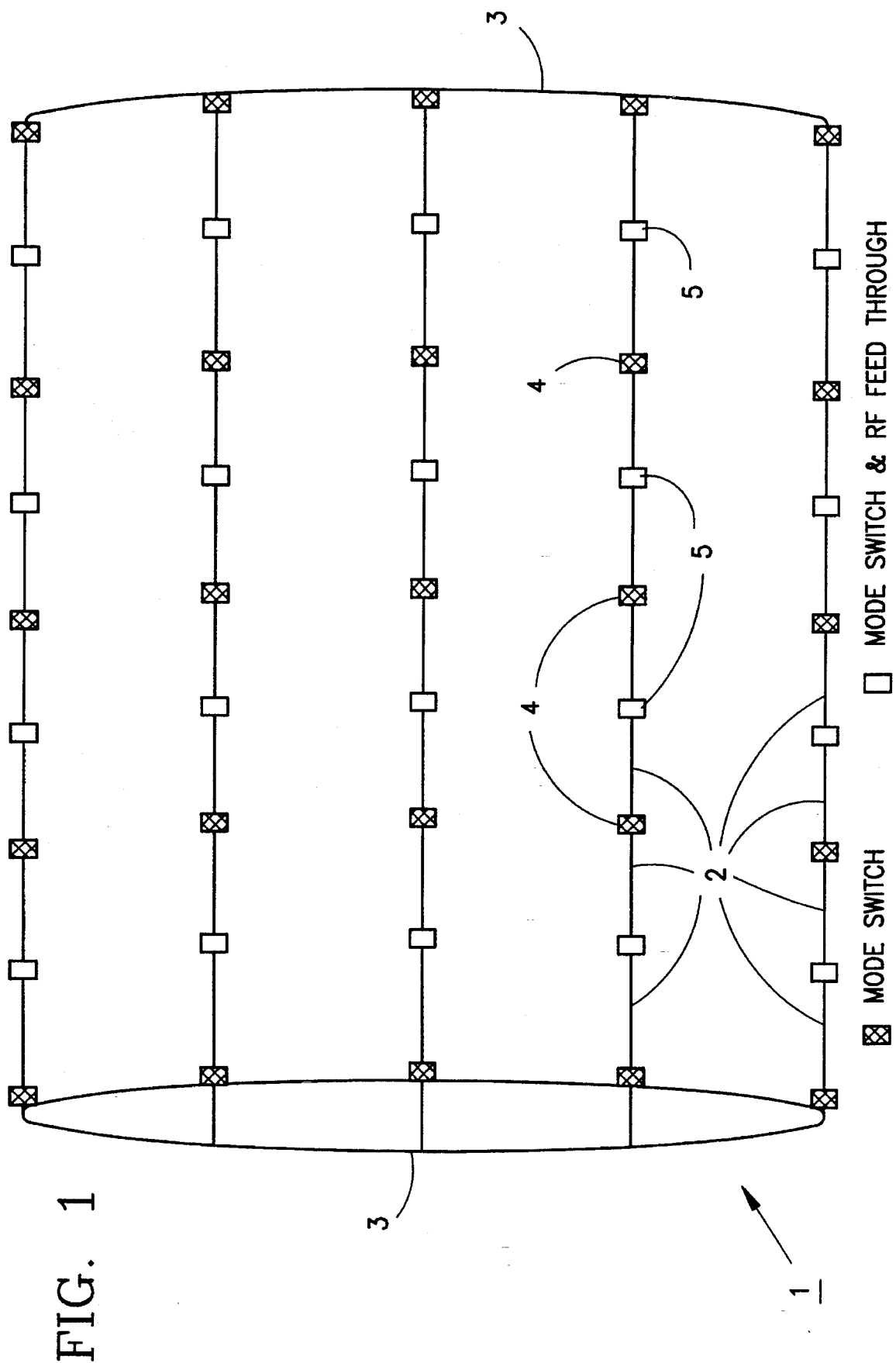
FIG. 1 is a schematic drawing of an MRI/hyperthermia body coil/dipole array constructed in accordance with the principles of a preferred embodiment of the invention.

Referring to FIG. 1, a preferred combination MRI/hyperthermia body coil and dipole antenna arrangement includes an array 1 of antenna elements 2 connected in a cylindrical configuration, the ends of the cylinder being defined by circular RF feed members 3. Circular RF members 3 are connected to a source of RF energy for supplying an MRI imaging field to the antenna elements when they are electrically connected together through mode switches 4 and mode switch/feedthrough elements 5.

The individual antenna elements 2 are simultaneously connected to each other via mode switches 4 and mode switches (described below) in the switch/RF feedthrough elements 5. When mode switches 4 and the mode switches in the RF feedthrough elements 5 are closed, energy is supplied from one of the circular RF feeds 3 through each of the antenna elements and switches to form a conventional MRI imaging apparatus. However, when the mode switches 4 and additional mode switches in the mode switch/RF feedthrough elements 5 are open, the antenna elements are disconnected from each other and instead are connected to individual sources of RF energy at frequencies suitable for hyperthermia treatment, the RF feedthroughs being individually controllable to focus RF energy on a selected area for hyperthermia treatment. By alternatively opening and closing the switches, the tissues targeted for hyperthermia treatment can be monitored in real time as treatment progresses.

Figure 2:
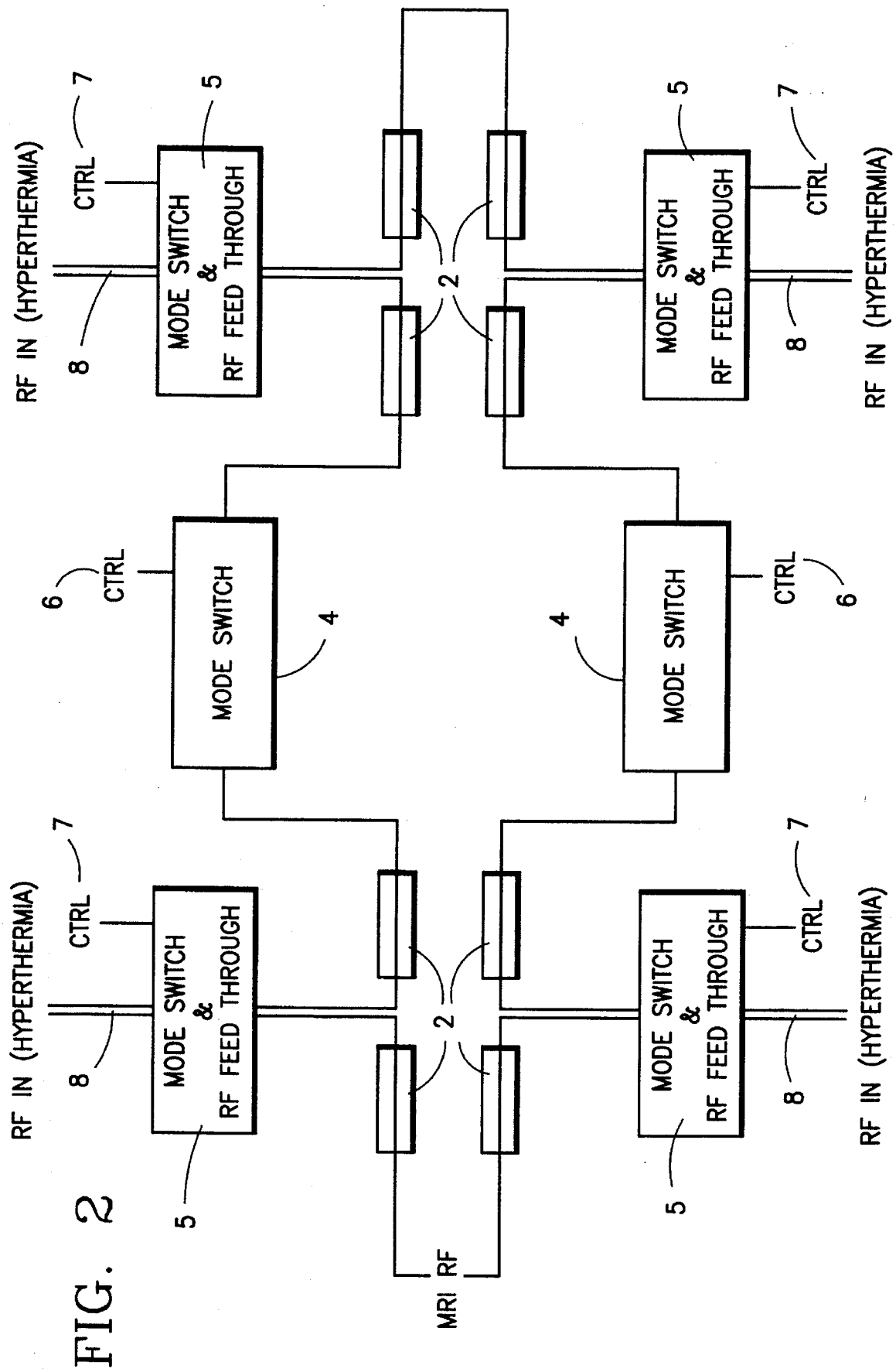
FIG. 2 is a block diagram showing the principal functional elements of the array of FIG. 1.

The operation of the system is illustrated in more detail in FIG. 2. When each of the mode switches 4 and 5 is closed by means of respective control signal inputs 6 and 7, RF energy flows through the antenna elements 2 and the switches in a complete circuit. However, when each of the switches is open, the individual elements form axially polarized dipole antennas to which an appropriate hyperthermia frequency may be selectively via RF inputs 8.

Examples of mode switches and mode switch/feedthrough elements suitable for use in the antenna configuration described above are shown in FIGS. 3 and 4. It should be appreciated by those skilled in the art, however, that numerous alternative mode switches and feedthroughs could be used in the arrangement of FIGS. 1 and 2, and that the invention is not intended to be limited to any particular switch or feedthrough design.

Figure 3:
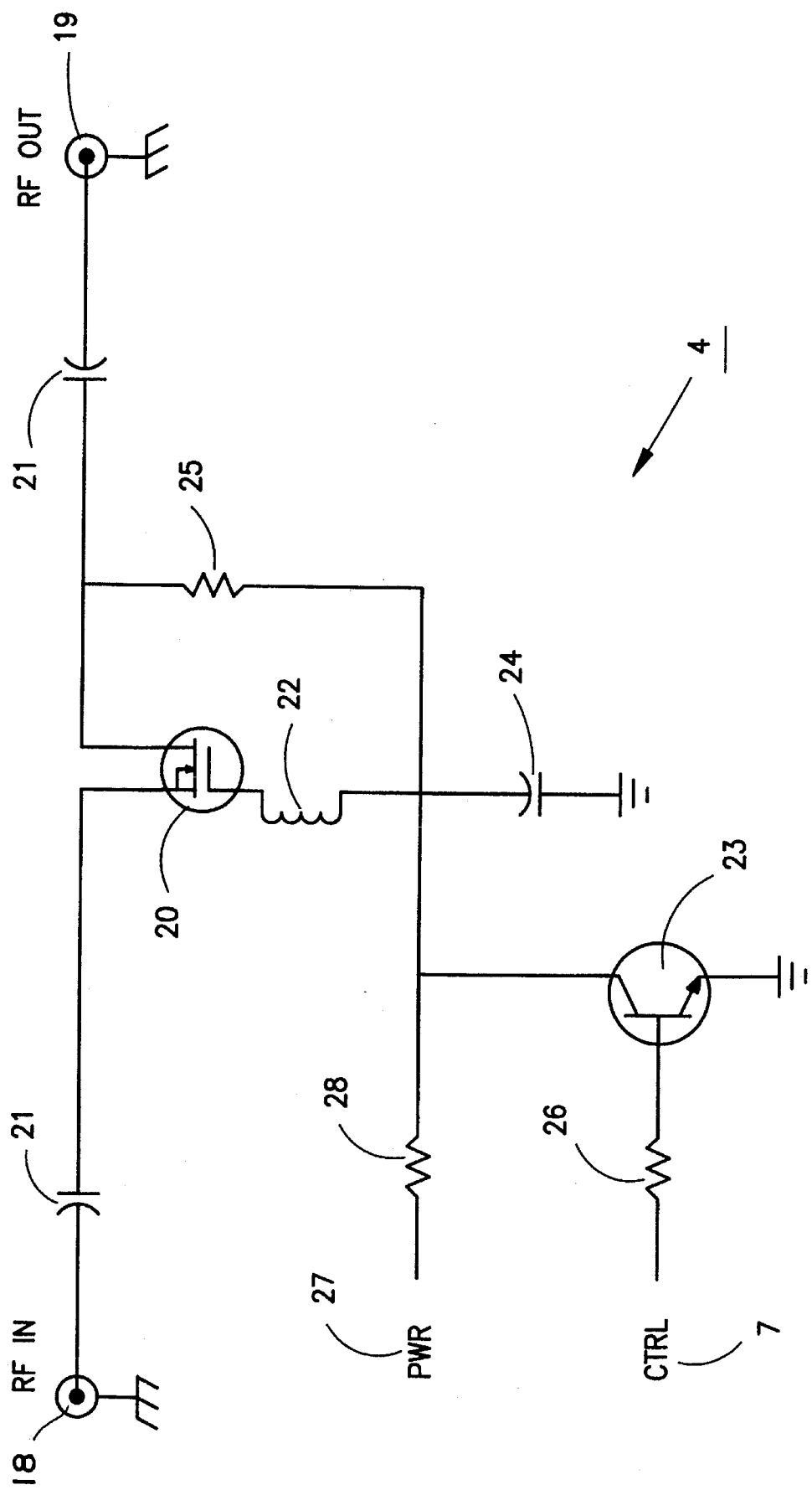
FIG. 3 is a schematic circuit diagram showing details of a preferred mode switch for use in the system of FIGS. 1 and 2.

The exemplary mode switch shown in FIG. 3 includes an RF input 18 and RF output 19 for receiving RF energy from and supplying RF energy to adjacent antenna elements at a frequency suitable for MRI imaging. The switch itself is preferably in the form of a VMOS field effect transistor 20 having a control electrode or gate connected to a bias power supply 27 through a resistor 28 and a bias circuit consisting of inductor 22, capacitor 25, and resistor 26 in known manner. The bias voltage, which controls whether transistor 21 is switched on or off, is provided by a bipolar transistor 23, the source and drain of transistor 20 being connected to the RF input and output. When transistor 23 is switched on by applying a control signal through resistor 26 to the base of the transistor, the collector and emitter of transistor 23 are shorted and the VMOS bias power supply is shunted to ground causing transistor 20 to be switched off.

Those skilled in the art will appreciate that the control signal applied to the base of transistor 23 may be supplied by a controller (not shown) programmed to alternate between hyperthermia and MRI configurations, either automatically or in response to operator input. Since hyperthermia energy is generally applied in the form of pulses, the MRI imaging can occur between the pulses and an image can thereby be obtained simultaneously with the treatment.

Figure 4:
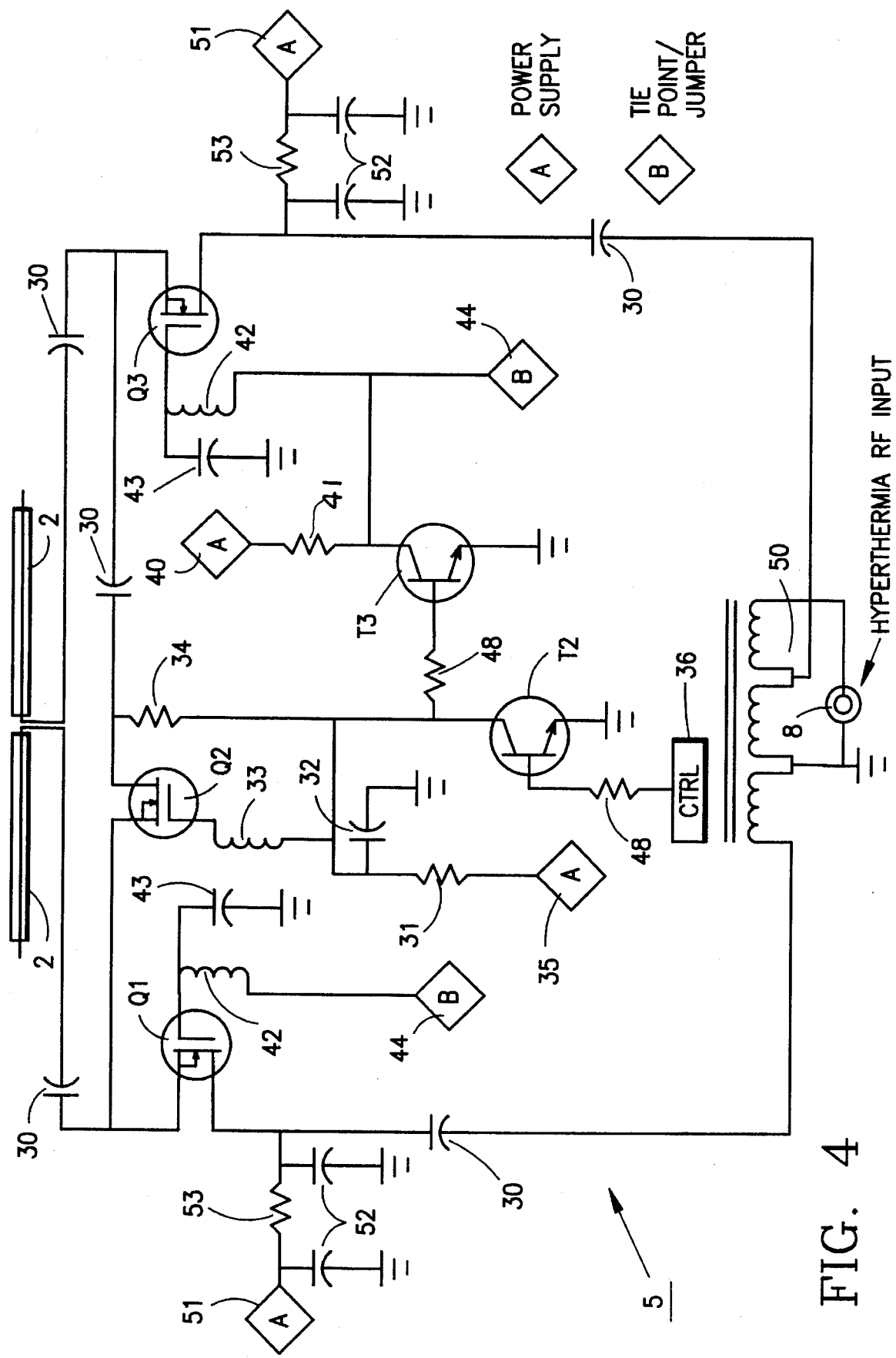
FIG. 4 is a schematic circuit diagram showing details of a preferred mode switch and RF feedthrough for the system of FIGS. 1 and 2.

The feedthrough switch illustrated in FIG. 4 includes a feedthrough VMOS field effect transistor Q2 having a gate connected to bias power supply 35 through a resistor 31 and to bipolar transistor T2 via bias circuitry including inductors 33 and 34, and a source and drain connected between adjacent antenna elements 2 via blocking capacitors 30. Like control transistor 23 of mode switch 4, the base of control transistor T2 is connected to receive control signals from a controller via input 36, preferably simultaneously with the supply of control signals to transistor 23, the application of the control signals causing the gate of the corresponding transistor Q2 to be connected to ground and thereby switched off.

When the bias voltage supplied by the control signal is switched to a low level, and transistor T2 is switched off, transistor Q2 is switched on, electrically connecting the source and drain to permit MRI RF energy to pass between the individual antenna elements 2 in the same manner as described above in connection with transistor 20. At this time, the MRI RF energy is supplied to all of the antenna elements in the cylindrical array. However, when a control signal is supplied to transistor T2, the bias power supply 35 for the gate of the corresponding switching transistor Q2 is connected to ground and transistor Q2 is thereby switched off, transistor T3, the base of which is connected to power supply 35 through a bias resistor 48, is also switched off, causing a bias voltage from power supply 40 to be applied via resistor 41 to the respective gates of VMOS field effect transistors Q1 and Q3 through bias inductors 42 and capacitors 43 (the latter via a jumper 44), as a result of which an RF input may selectively be applied through transformer 50 to the pairs of individual antenna elements controlled by the feedthrough to form axially polarized dipole antenna elements. Finally, additional power supplies 51 filtered by capacitors 52 and resistor 53 are provided to establish a DC offset for the hyperthermia signal.

In summary, each of the exemplary mode switches 4 is controlled by supplying a bias voltage to a bipolar transistor 23, which in turn controls the gate of a VMOS transistor 20 to selectively connect and disconnect adjacent antenna elements from each other depending on the control signal. The control signal also supplies a bias voltage to a transistor T1 in each of the mode switch/RF feedthrough elements 5, transistor T1 in turn controlling the gates of a VMOS transistor Q2 to selectively connecting and disconnecting adjacent antenna elements from each other, and also the gates of respective VMOS transistors Q1 and Q2 for permitting hyperthermia energy to be separately supplied to the individual antenna elements, the antenna elements having been disconnected from each other by the switching off of transistors 20 and Q2.

Having thus described a particular preferred embodiment of the invention in sufficient detail to enable those skilled in the art to make and use the invention, it will be appreciated by those same skilled in the art that numerous variations and modifications of the preferred embodiment are possible within the spirit and scope of the invention, and consequently it is intended that the invention not be limited to the illustrated embodiments, but that the invention be defined solely by the appended claims.

We claim:

1. MRI/hyperthermia dual function antenna apparatus, comprising:

a plurality of antenna elements;

switch means for selectively connecting and disconnecting said antenna elements to and from each other;

MRI RF energy supply means for supplying MRI RF energy collectively to said antenna elements when they are connected together by said switch means; and feedthrough means for supplying hyperthermia RF energy individually to ones of said antenna elements when they are disconnected from each other by said switch means.

2. Apparatus as claimed in claim 1, wherein said antenna elements are arranged to form a cylindrical whole body MRI imaging antenna when said antenna elements are electrically connected together by said switch means.

3. Apparatus as claimed in claim 1, wherein said feedthrough means is arranged to selectively supply hyperthermia RF energy to pairs of said antenna elements to from axially polarized dipole antennas when said antenna elements are electrically disconnected form each other by said switch means.

4. A method of hyperthermia treatment, comprising the steps of:

a.) controlling switches to electrically connect a plurality of antenna elements to each other to form an MRI RF antenna array;

b.) supplying MRI RF energy to all of the antenna elements in the array when the antenna elements are connected together in order to cause the antenna elements to direct MRI RF energy at a patient and thereby permit MR imaging of the patient for the purpose of monitoring a temperature of targeted and surrounding tissues in a patient during the hyperthermia treatment;

c.) controlling the switches to electrically disconnect the antenna elements from each other; and d.) selectively supplying hyperthermia RF energy to pairs of the antenna elements when the antenna elements are disconnected from each other in order to cause the antenna elements to direct hyperthermia RF energy doses at the patient for the purpose of heating the targeted tissues during the hyperthermia treatment.

\* \* \* \* \*